US007625927B2

(12) United States Patent
Klimko et al.

(10) Patent No.: US 7,625,927 B2
(45) Date of Patent: Dec. 1, 2009

(54) METHOD OF TREATING GLAUCOMA

(75) Inventors: Peter G. Klimko, Fort Worth, TX (US); Iok-Hou Pang, Grand Prairie, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 11/679,629

(22) Filed: Feb. 27, 2007

(65) Prior Publication Data

US 2007/0203174 A1    Aug. 30, 2007

Related U.S. Application Data

(60) Provisional application No. 60/777,065, filed on Feb. 27, 2006.

(51) Int. Cl.
*A61K 31/47* (2006.01)
(52) U.S. Cl. .................. 514/309; 514/307; 514/913
(58) Field of Classification Search .................. 514/307, 514/309, 912
See application file for complete search history.

(56) References Cited

U.S. PATENT DOCUMENTS

| | | | |
|---|---|---|---|
| 4,550,022 A | 10/1985 | Garabedian et al. | |
| 5,049,586 A | 9/1991 | Ortega et al. | |
| 5,620,995 A | 4/1997 | Weidmann et al. | |
| 5,719,164 A | 2/1998 | Weidmann et al. | |
| 5,916,898 A | 6/1999 | Edwards et al. | |
| 5,952,378 A | 9/1999 | Stjernschantz et al. | |
| 6,020,350 A * | 2/2000 | Weidmann et al. ........... | 514/346 |
| 6,093,730 A | 7/2000 | Weidmann et al. | |
| 6,441,047 B2 * | 8/2002 | DeSantis, Jr. ................ | 514/649 |
| 2004/0235082 A1 | 11/2004 | Fourney et al. | |
| 2004/0254215 A1 | 12/2004 | Arend et al. | |

FOREIGN PATENT DOCUMENTS

| | | |
|---|---|---|
| DE | 197 46 287 | 4/1999 |
| EP | 0 661 269 | 7/1995 |
| EP | 0 765 871 | 4/1997 |
| EP | 0 846 685 | 6/1998 |
| WO | 99/21860 | 5/1999 |
| WO | 2004/052284 | 6/2004 |
| WO | 2004/052285 | 6/2004 |
| WO | 2004/108681 | 12/2004 |
| WO | 2005/034929 | 4/2005 |

OTHER PUBLICATIONS

Anderson et al., "Effect of Intraocular Pressure on Rapid Axoplasmic Transport in Monkey Optic Nerve", IOVS, vol. 13(10):771-783, 1974.
Arita et al., "Resolvin E1, An Endogenous Lipid Mediator Derived from Omega-3 Eicosapentaenoic Acid, Protects Against 2,4,6-Trinitrobenzene Sulfonic Acid-Induced Colitis", PNAS, vol. 102(21):7671-7676, May 2005.
Arjamaa et al., "Oxygen-Dependent Diseases in the Retina: Role of Hypoxia-Inducible Factors", Experimental Eye Research, vol. 83(3):473-483, Sep. 2006.
Butler, D., "Cheaper Approaches to Flu Divide Researchers", Nature, vol. 448:976-977, Aug. 2007.
Clark et al., "Ophthalmic Drug Discovery", Nature Reviews—Drug Discovery, vol. 2(6):448-459, Jun. 2003.
Esquenazi et al., "Topical Combination of NGF and DHA Increases Rabbit Corneal Nerve Regeneration After Photorefractive Keratectomy", IOVS, vol. 46(9):3121-3127, Sep. 2005.
Fahy et al., "A Comprehensive Classification System for Lipids1", Journal of Lipid Research, vol. 46:839-861, 2005.
Fiorucci et al., "A B-Oxidation-Resistant Lipoxin A4 Analog Treats Hapten-Induced Colitis by Attenuating Inflammation and Immune Dysfunction," PNAS, vol. 101(44):15736-15741, Nov. 2004.
Gewirtz et al., "Lipoxin A4 Analogs Attenuate Induction of Intestinal Epithelial Proinflammatory Gene Expression and Reduce the Severity of Dextran Sodium Sulfate-Induced Colitis", Journal of Immunology, vol. 168(10):5260-5267, 2002.
Gronert et al., "A Role for the Mouse 12/15-Lipoxygenase Pathway in Promoting Epithelial Wound Healing and Host Defense", Journal of Biological Chemistry, vol. 280(15):15267-15278, 2005.
Guilford et al., "Novel 3-Oxa Lipoxin A4 Analogues with Enhanced Chemical and Metabolic Stability Have Anti-inflammatory Activity in Vivo", J. Medicinal Chemistry, vol. 47:2157-2165, 2004.
Hashimoto et al., "Long-term activation of c-Fos and c-Jun in Optic Nerve Head Astrocytes in Experimental Ocular Hypertension in Monkeys and After Exposure to Elevated Pressure in Vitro", Brain Research, vol. 1054(2):103-115, 2005.
Hirsila et al., "Characterization of the Human Prolyl 4-Hydroxylases that Modify the Hypoxia-inducible Factor", Journal of Biological Chemistry, vol. 278(33):30772-30780, 2003.
Ivan et al., "Biochemical Purification and Pharmacological Inhibition of a Mammalian Prolyl Hydroxylase Acting on Hypoxia-Inducible Factor", PNAS, vol. 99(21):13459-13464, Oct. 2002.
Kaplan et al., "Signal Transduction by the Neurotophin Receptors", Current Opinion in Cell Biology, vol. 9:213-221, 1997.
Kuehn et al., "Retinal Ganglion Cell Death in Glaucoma: Mechanisms and Neuroprotective Strategies", Ophthalmology Clinics of North America, vol. 18(3):383-395, 2005.
Kwong et al, "Expression of Phosphorylated c-Jun N-terminal Protein Kinase (JNK) in Experimental Glaucoma in Rats", Experimental Eye Research, vol. 82(4):576-582, 2006.
Lee et al., "Glaucoma and its Treatment: A Review", Am. J. Health System Pharm., vol. 62(7):691-699, 2005.
Lee et al., "Neuronal Apoptosis Linked to EgIN3 Prolyl Hydroxylase and Familial Pheochromocytoma Genes: Development Culling and Cancer", Cancer Cell, vol. 8(2):155-167, Aug. 2005.
Levy et al., "Expression of BPI (bactericidal/permeability-increasing protein) in Human Mucosal Epithelial", Biochemical Society Transactions, vol. 31(4):795-800, 2003.

(Continued)

*Primary Examiner*—Zohreh A Fay
(74) *Attorney, Agent, or Firm*—Mark E. Flanigan

(57) ABSTRACT

Described are methods for the treatment of ocular hypertension or glaucoma comprising administering a pharmaceutically effective amount of one or more compounds that inhibit the enzyme EgLN-3. Certain embodiments of the invention combine the use of EgLN-3 with other glaucoma treatment agents. The compounds of the invention may be formulated in compositions comprising pharmaceutically acceptable carriers.

9 Claims, 1 Drawing Sheet

OTHER PUBLICATIONS

Lewin et al., "Physiology of the Neurotrophins", Ann. Rev. Neuroscience, vol. 19:289-317, 1996.

Lipscomb et al., "SM-20 Is a Novel Mitochondrial Protein That Causes Caspase-Dependent Cell Death in Nerve Growth Factor-dependent Neurons", Journal of Biological Chemistry, vol. 276(7):5085-5092, 2001.

Lipscomb et al., "Expression of the SM-20 Gene Promotes Death in Nerve Growth Factor-Dependent Sympathetic Neurons", Journal Neurochemistry, vol. 73(1):429-432, 1999.

Lotzer et al., "The 5-Lipoxygenase Pathway in Arterial Wall Biology and Atherosclerosis", Biochimica et Biophysica Acta, vol. 1736(1):30-37, 2005.

Lukiw et al., "A Role for Docosahexaenoic Acid-Derived Neuroprotection D1 in Neural Cell Survival and Alzheimer Disease", Journal of Clinical Investigation, vol. 115(10):2774-2783, Oct. 2005.

Mansour-Robaey et al., "Effects of Ocular Injury and Administration of Brain-Derived Neurotrophic Factor on Survival and Re-growth of Axotomized Retinal Ganglion Cells", PNAS, vol. 91(5):1632-1636, Mar. 1994.

Meyer-Franke et al., "Characterization of the Signaling Interactions that Promote the Survival and Growth of Developing Retinal Ganglion Cells in Culture", Neuron, vol. 15(4), 805-819, Oct. 1995.

Mukherjee et al., "Neuroprotection D1: A Docosahexaenoic Acid-Derived Docosatriene Protects Human Retinal Pigment Epithelial Cells From Oxidative Stress", PNAS, vol. 101(22):8491-8496, Jun. 2004.

Peso et al., "The von Hippel Lindau/Hypoxia-inducible Factor (HIF) Pathway Regulates the Transcription of HIF-Proline Hydroxylase Genes in Response to Low Oxygen", Journal of Biological Chemistry, vol. 278(49):48690-48695, Dec. 2003.

Quigley et al., "The Dynamics and Location of Axonal Transport Blockade by Acute Intraocular Pressure Elevation in Primate Optic Nerve", IOVS, vol. 15(8):606-616, Aug. 1976.

Quigley et. al., "The Transcription Factor C-Jun is Activated in Retinal Ganglion Cells in Experimental Rat Glaucoma", Experimental Eye Research, vol. 80(5):663-670, 2005.

Schlingensiepen et al., "The Role of Jun Transcription Factor Expression and Phosphorylation in Neuronal Differentiation, Neuronal Cell Death, and Plastic Adaptations in Vivo", Cellular & Molecular Neurobiology, vol. 14 (5):487-505, 1994.

Segal R.A., "Selectivity in Neurotrophin Signaling: Theme and Variations", Annual Review Neuroscience, vol. 26:299-330, 2003.

Sowers et al., "The Effects of Cyclooxygenase-2 Inhibitors and Nonsteroidal Anti-inflammatory Therapy on 24-Hour Blood Pressure in Patients with Hypertension, Osteoarthritis, and Type 2 Diabetes Mellitus", Archives of Internal Medicine, vol. 165(2):161-168, 2005.

Straub et al., "Induction of SM-20 in PC12 Cells Leads to Increased Cytochrome c Levels, Accumulation of Cytochrome c in the Cytosol, and Caspase-Dependent Cell Death", Journal of Neurochemistry, vol. 85(2):318-328, 2003.

Wallace et al., "Lipoxins in Gastric Mucosal Health and Disease", Prostaglandins, Leukotrienes and Essential Fatty Acids, vol. 73(3-4):251-255, 2005.

Wang et al., "Factors Contribution to Neuronal Degeneration in Retinas of Experimental Glaucomatous Rats", Journal of Neuroscience Research, vol. 82(5):674-678, 2005.

Wilson, R.P., "Anesthesia", Ophthalmic Surgery: Principles of Practice, Edited by G. L. Spaeth, MD, W. B. Sanders Co., Philadelphia, Pa., U.S.A., Chapter 5:85-87, 1990.

Wong et al., "Cardiovascular Hazard and Non-Steroidal Anti-Inflammatory Drugs", Current Opinion in Pharmacology, vol. 5:204-210, 2005.

* cited by examiner

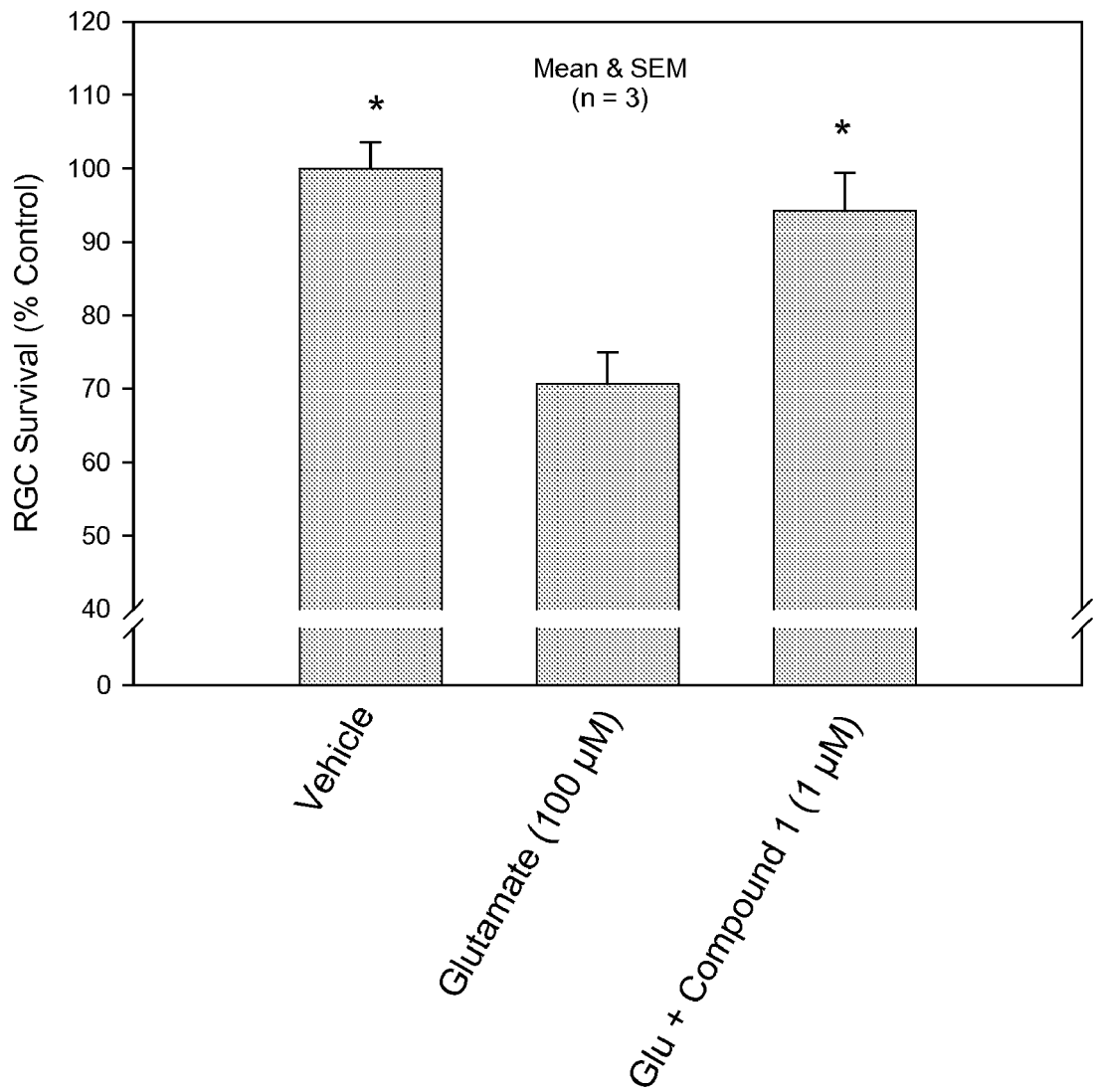
Figure 1. Effects of Compound 1 on the survival of cultured adult rat RGCs. The cells were treated with glutamate (100 µM) with or without Compound 1 for 3 days. * represents statistical significance ($p < 0.05$) vs. the glutamate-treated group by One-way ANOVA followed by Dunnett's test.

METHOD OF TREATING GLAUCOMA

CROSS-REFERENCE TO RELATED APPLICATION

This application claims priority under 35 U.S.C. § 119 to U.S. Provisional Patent Application No. 60/777,065, filed Feb. 27, 2006, the entire contents of which are incorporated herein by reference.

TECHNICAL FIELD OF THE INVENTION

The present invention is directed to the treatment of ocular disorders. In particular, the present invention is directed toward the use of compounds that inhibit the enzyme EgLN-3 to treat glaucoma in mammals.

BACKGROUND OF THE INVENTION

Primary open-angle glaucoma (POAG) is a progressive disease leading to optic nerve damage and, ultimately, loss of vision. The cause of this disease has been the subject of extensive studies for many years, but is still not fully understood. Glaucoma results in the neuronal degeneration of the retina and optic nerve head, a gradual loss of retinal ganglion cells ("RGCs"), a decline of visual function, and ultimately blindness [Clark et al., *Nature Reviews Drug Discovery*, 2003, Vol. 2(6):448-459].

Several theories have been proposed to elucidate the etiology of glaucoma. One theory suggests that excessive intraocular pressure (IOP), which in some cases may be coupled with genetic defects on the optic nerve head, disrupts the normal axonal transport along the optic nerve and leads to RGC injury. Glaucoma treatment via reduction in IOP is frequently achieved with prescription eye drops containing therapeutic agents that suppress aqueous humor production. These agents include beta-blockers, such as timolol and betaxolol, and carbonic anhydrase inhibitors, such as dorzolamide and brinzolamide. Recently the use of prostaglandin analogs, such as latanoprost, bimatoprost and travoprost, which are believed to reduce IOP by increasing uveoscleral outflow, has become common. In cases where drug therapy is ineffective, treatment with lasers or surgery to reduce IOP may be required [Lee et al., *Am. J. Health Syst Pharm.*, 2005, Vol. 62(7):691-699].

Disturbance of axonal transport of the optic nerve hinders traffic of intracellular molecules between the RGC soma and its terminal. Among the intracellular molecules of importance are neurotrophic factors. Neurotrophic factors are peptide molecules which stimulate or otherwise maintain growth of neural tissue. The transport of neurotrophic factors from the brain to the cell body of RGCs is essential to the survival of the RGCs. Deprivation of neurotrophic factors can induce apoptosis of neurons, and may be a cause of glaucoma-induced RGC apoptosis; see for example: Kuehn et al., *Ophthalmol. Clin. North Am.*, 2005, Vol. 18(3):383-395; Anderson et al., *Invest. Ophthalmol.*, 1974, Vol. 13(10):771-783; Quigley et al.,*Invest. Ophthalmol.*, 1976,Vol. 15(8):606-616; Mansour-Robaey et al.,*Proc. Natl. Acad. Sci. USA*, 1994,Vol. 91(5):1632-1636; Meyer-Franke et al., *Neuron* 1995, Vol. 15(4):805-819.

The neurotrophin ("NT") family of peptides include nerve growth factor (NGF), brain-derived neurotrophic factor (BDNF), NT-3, NT-4/5 and NT-6. They act by binding to neuron surface receptors, such as TrkA, TrkB, and TrkC. The Trk receptors are tyrosine kinases. TrkA is selective for NGF, TrkB is selective for both BDNF and NT-4/5, whereas TrkC is selective for NT-3. After binding, the NT-receptor complex is internalized and transported via the axon to the soma. These receptors undergo ligand-induced phosphorylation and dimerization, and activate a cascade of Ras protein-mediated signal transduction events that affect multiple vital functions of the neuron (Lewin et al., *Ann. Rev. Neurosci.*, 1996, Vol. 19:289-317; Segal, R. A., *Annu. Rev. Neurosci.*, 2003, Vol. 26:299-330; Kaplan et al., *Curr. Opin. Cell Biol.*, 1997, Vol. 9(2):213-221]. Thus, these receptors play a fundamental role in the regulation of survival and differentiation of developing neurons and contribute to the maintenance of neuronal machinery in adult life.

The EgLN enzyme family are 2-oxoglutarate-dependent prolyl hydroxylases that catalyze the constitutive hydroxylation of the HIF-1α protein under normoxic conditions [Peso et al., *J. Biol. Chem.*, 2003, Vol. 278(49):48690-48695; Ivan et al., *PNAS*, 2002, Vol. 99(21):13459-13464]. The hydroxylated HIF-1α protein is targeted for polyubiquination and proteasomal degradation by pVHL, the protein product of the von Hippel-Landau gene. Under hypoxic conditions, oxygen concentration becomes rate-limiting and EgLN-catalyzed hydroxylation is inefficient. Consequently HIF-1α escapes destruction and forms a heterodimer with HIF-1β. The complex is transported to the nucleus, where it acts as a transcription factor to up-regulate production of hypoxia-induced proteins and growth factors, such as vascular endothelial growth factor (VEGF).

The EgLN-3 isozyme also appears to be involved as an effector of apoptosis in sympathetic neurons under certain conditions. In particular, EgLN-3 is a downstream effector of nerve growth factor (NGF) withdrawal-induced apoptosis in NGF-dependent neurons. Expression of SM-20, a rat ortholog of EgLN-3, increases after NGF withdrawal in sympathetic neurons [Lipscomb et al., *J. Neurochem.* 1999, Vol. 73(1)429-432]. Induced expression of SM-20 causes apoptosis in sympathetic neurons even in the presence of NGF in a caspase-dependent process [*J. Neurochem.*, 2003, Vol. 85(2): 318-328]. Although SM-20 is normally resident in the mitochrondria, a truncated form that localizes to the cytoplasm due to loss of a mitochondrial targeting sequence still induces apoptosis [Lipscomb et al., *J Biol. Chem.* 2001, Vol. 276(7): 5085-5092].

These findings have recently been extended to developing neurons [Lee et al., *Cancer Cell*, 2005, Vol. 8:155-167]. During embryogenesis, sympathetic neuronal precursor cells that fail to make synaptic connections are starved of NGF and undergo c-Jun-dependent apoptosis [Schlingensiepen et al., *Cell. Mol. Neurobiol.*, 1994, Vol. 14:487-505]. The risk of a type of neuronal cancer called familial pheochromocytoma is increased by germline mutations that inactivate pVHL or NF1 (an antagonist of the NGF receptor TrkA), or that activate c-RET (the receptor for glial derived neurotrophic factor, which cross-talks with TrkA). In each of these cases the intracellular concentration of the c-Jun antagonist JunB increases, inhibiting apoptosis. Germline mutations that reduce the activity of succinate dehydrogenase (SDH) also increase familial pheochromocytoma risk. Succinate is a co-product of EgLN-3-catalyzed proline hydroxylation and feedback inhibits the enzyme, and thus needs to be removed by SDH for EgLN-3 prolyl hydroxylase activity. Sporadic pheochromocytoma due to somatic mutation in one of these genes is rare since apoptosis of "unconnected" sympathetic neuronal precursor cells is not important once embryogenesis is complete.

NGF withdrawal-induced apoptosis requires EgLN-3 proline hydroxylase activity. EgLN-3-induced cell death is not reduced by co-expression of JunB. Additionally, EgLN-3 expression knockdown by siRNA inhibits c-Jun induced cell death. These observations indicate that EgLN-3 is necessary and sufficient for NGF withdrawal-induced apoptosis, and acts downstream of c-Jun. The presumed protein target of EgLN-3-catalyzed proline hydroxylation that is important for apoptosis induction has not been identified, although it is suspected that pVHL's polyubiquination (and subsequent marking for proteasomal destruction) of a hyperphosphorylated form of atypical protein kinase C is responsible for pVHL's suppression of JunB.

Induction of neuronal apoptosis via c-Jun N-terminal kinase (JNK)-catalyzed phosphorylation of c-Jun has been implicated as a contributing factor to retinal ganglion cell (RGC) death in high IOP-induced glaucoma models in monkeys [Hashimoto et al., *Brain Research*, 2005, Vol. 1054(2): 103-115] and rats [Quigley et al., *Exp Eye Res.* 2005, Vol. 80(5):663-670; Wang et al., *J Neurosci Res.*, 2005, Vol. 82(5): 674-678; Kwong et al., *J. Exp. Eye. Res.*, 2006, Vol. 82(4): 576-582]. It is not known how important NGF withdrawal is the pathological progression of RGC loss in POAG, nor whether EgLN-3 can act via the JNK pathway to induce neuronal cell death.

SUMMARY OF THE INVENTION

The present invention is directed in part to methods for the treatment of glaucoma and ocular hypertension. According to one embodiment of the present invention, an inhibitor of the EgLN-3 enzyme is administered to a patient suffering from glaucoma or ocular hypertension. The present invention further discloses compositions and methods for systemic, topical, and intraocular administration of an EgLN-3 inhibitor.

Without intending to be bound by any theory, it is believed that the compounds of the present invention treat ocular hypertension and glaucoma by inhibiting RGC cell death induced by trophic factor withdrawal, by inhibiting activation of the c-Jun/JNK pathway, and by inhibiting deposition of extracellular matrix in the trabecular meshwork via reducing conversion of procollagen to collagen.

The foregoing brief summary broadly describes the features and technical advantages of certain embodiments of the present invention. Additional features and technical advantages will be described in the detailed description of the invention that follows. Novel features which are believed to be characteristic of the invention will be better understood from the detailed description of the invention when considered in connection with any accompanying examples. However, examples provided herein are intended to help illustrate the invention or assist with developing an understanding of the invention, and are not intended to be definitions of the invention's scope.

BRIEF DESCRIPTION OF THE DRAWINGS

A more complete understanding of the present invention and the advantages thereof may be acquired by referring to the following description, taken in conjunction with the accompanying drawing in which like reference numbers indicate like features and wherein:

FIG. 1 is a bar graph showing the effects of Compound 1 on the survival of cultured adult rat retinal ganglion cells (RGCs).

DETAILED DESCRIPTION OF THE INVENTION

Unless indicated otherwise, all component amounts are presented on a % (w/v) basis.

The present invention generally provides EgLN-3 inhibitory compounds used as treatments for ocular hypertension or glaucoma. In one embodiment a composition comprising one or more compounds of formulae A-H (shown below) is administered to a patient suffering from or at risk of suffering from ocular hypertension or glaucoma.

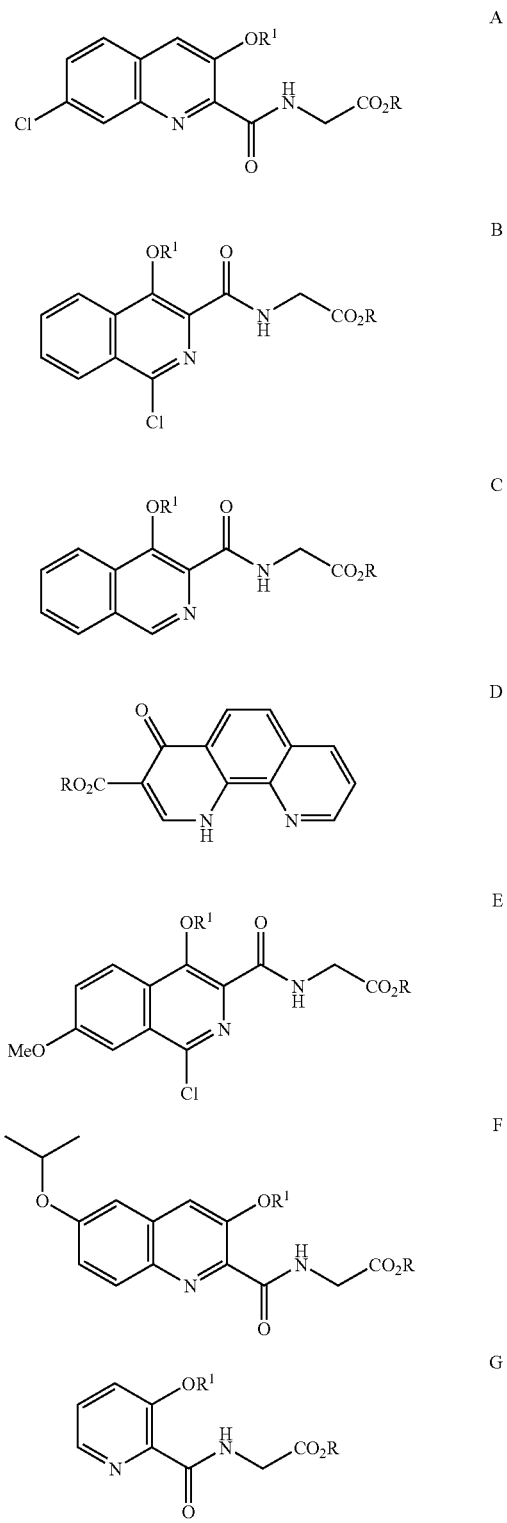

-continued

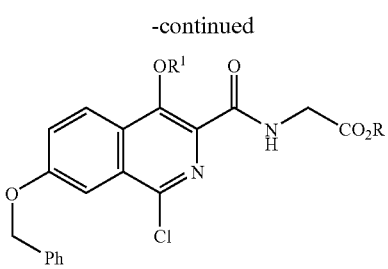

H wherein:
R is H, $C_{1-6}$ straight chain or branched alkyl, phenyl, or benzyl, or $CO_2R$ forms a salt of formula $CO_2^-M^+$, with $M^+$ being $Li^+$, $Na^+$, $K^+$, or $NH_4^+$; and
$R^1$ is H, $C(O)CH_3$, or $C(O)C_6H_5$.

Preferred are compounds of formulae A-H with R being H, $CH_3$, $C_2H_5$, or i-$C_3H_7$, and $R^1$ being H or $C(O)CH_3$. Especially preferred are compounds B and G with R being H, $CH_3$, $C_2H_5$, or i-$C_3H_7$, and $R^1$ being H or $C(O)CH_3$.

The use of some of the compounds of the present invention for the treatment of obesity (Fourney et al., U.S. Published Patent Application US2004/0235082A1), anemia via increasing endogenous erythropoietin production (Arend et al., U.S. Published Patent Application US2004/0254215A1), and fibrotic diseases (Weidmann et al., U.S. Pat. Nos. 6,093,730 and 5,719,164), have been disclosed. Additionally, the use of the compounds of formula G with R=H and $R^1$=an alkyl group has been disclosed for the postoperative treatment of glaucoma operations (ostensibly to maintain the filtration bleb) (Wiedmann et al., U.S. Pat. No. 6,020,350). However the use of the compounds of the present invention for the treatment of glaucomatous optic neuropathy or as IOP-lowering agents has not been disclosed.

The compounds of formulae A-H with both R and $R^1$=H can be synthesized according to the following literature examples tabulated below and herein incorporated by reference.

| Compound Formula | Synthesis Reference |
|---|---|
| A | Weidmann et al., U.S. Pat. No. 5,719,164 |
| B | Weidmann et al., U.S. Pat. No. 6,093,730 |
| C | Arend et al., US Published Patent Application 2004/0254215 A1 |
| D | Edwards et al., U.S. Pat. No. 5,916,898 |
| E | Weidmann et al., U.S. Pat. No. 6,093,730 |
| F | Weidmann et al., U.S. Pat. No. 5,719,164 |
| G | Weidmann et al., U.S. Pat. No. 5,620,995 |
| H | Weidmann et al., U.S. Pat. No. 6,093,730 |

The EgLN-3 inhibitors of the present invention may be contained in various types of pharmaceutical compositions, in accordance with formulation techniques known to those skilled in the art. For example, the compounds may be included in tablets, capsules, solutions, suspensions, and other dosage forms adapted for oral administration; solutions and suspensions adapted for parenteral use; and solutions and suspensions adapted for topical ophthalmic, depot, or intraocular injection. Solutions, suspensions, and other dosage forms adapted for depot, oral, intra-ocular injection, and topical ophthalmic administration, such as eye drops and tissue irrigating solutions, are particularly preferred for the prevention or treatment of acute or chronic retinal or optic nerve head damage. Compositions can also be delivered topically to the eye according to the teachings in U.S. Pat. No. 5,952,378, which is herein incorporated by reference.

According to certain methods of the present invention, one or more compounds of formulae A-H can be administered in a pharmaceutically acceptable carrier or implant. Also, the compound(s) of formulae A-H can be administered topically in the form of an eye drop. The compositions and implants are formulated in accordance with methods known in the art. Additionally, the compositions and implants may contain a second drug, other than a compound of formulae A-H.

When the EgLN-3 inhibitors of the present invention are administered through means such as retrobulbar or periocular injection and intraocular perfusion or injection, the use of balanced salt irrigating solutions as vehicles are most preferred. BSS® Sterile Irrigating Solution and BSS Plus® Sterile Intraocular Irrigating Solution (Alcon Laboratories, Inc., Fort Worth, Tex., USA) are examples of physiologically balanced intraocular irrigating solutions. The latter type of solution is described in U.S. Pat. No. 4,550,022 (Garabedian, et al.), the entire contents of which are hereby incorporated in the present specification by reference. Retrobulbar and periocular injections are known to those skilled in the art and are described in numerous publications including, for example, *Ophthalmic Surgery: Principles of Practice*, Ed., G. L. Spaeth, W. B. Sanders Co., Philadelphia, Pa., U.S.A., pg. 85-87, 1990.

The compositions and implants used in the methods of the present invention contain a pharmaceutically effective amount of a compound of formulae A-H. Generally, the topically administrable compositions used in the methods of the present invention will contain from 0.001 to 2% of a compound of formulae A-H. Preferably, the compositions of the present invention will contain from 0.01 to 1% of a compound of formula A-H.

The topical compositions administered according to the present invention may also include various other ingredients, including but not limited to surfactants, tonicity agents, buffers, preservatives, co-solvents and viscosity building agents.

The compounds of the present invention can also be used in combination with other glaucoma treatment agents, such as, but not limited to, β-blockers, prostaglandin analogs, carbonic anhydrase inhibitors, $\alpha_2$ agonists, miotics, rho kinase inhibitors, and neuroprotectants.

Various tonicity agents may be employed to adjust the tonicity of the composition, preferably to that of natural tears for ophthalmic compositions. For example, sodium chloride, potassium chloride, magnesium chloride, calcium chloride, dextrose and/or mannitol may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm).

An appropriate buffer system (e.g., sodium phosphate, sodium acetate, sodium citrate, sodium borate or boric acid) may be added to the compositions to prevent pH drift under storage conditions. The particular concentration will vary, depending on the agent employed. Preferably, however, the buffer will be chosen to maintain a target pH within the range of pH 5.5-8.

Topical ophthalmic products are typically packaged in multidose form. Preservatives are typically required to prevent microbial contamination during use. Suitable preservatives include: benzalkonium chloride, chlorobutanol, benzododecinium bromide, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/v. Unit dose compositions of the present invention will be sterile, but typically will not contain a preservative and will be unpreserved.

Generally, 1-2 drops of topical compositions containing one or more compounds of formulae A-H will be administered from 1-3 times per day.

The following Examples 1 and 2 are formulations useful for intraocular, periocular, or retrobulbar injection or perfusion.

EXAMPLE 1

| Component | % w/v |
| --- | --- |
| Compound of formulae A-H | 0.1 |
| Dibasic sodium phosphate | 0.2 |
| HPMC | 0.5 |
| Polysorbate 80 | 0.05 |
| Benzalkonium chloride | 0.01 |
| Sodium chloride | 0.75 |
| Edetate disodium | 0.01 |
| NaOH/HCl | q.s. to pH 7.4 |
| Purified water | q.s. to 100% |

EXAMPLE 2

| Component | % w/v |
| --- | --- |
| Compound of formulae A-H | 0.1 |
| Cremophor EL | 10 |
| Tromethamine | 0.12 |
| Boric acid | 0.3 |
| Mannitol | 4.6 |
| Edetate disodium | 0.1 |
| Benzalkonium chloride | 0.1 |
| NaOH/HCl | q.s. to pH 7.4 |
| Purified water | q.s. to 100% |

EXAMPLE 3

The following tablet formulation can be made pursuant to U.S. Pat. No. 5,049,586, incorporated herein by reference.

| Component | % w/v |
| --- | --- |
| Compound of formulae A-H | 60 |
| Magnesium oxide | 20 |
| Corn starch | 15 |
| Polyvinylpyrrolidone | 3 |
| Sodium carboxymethylcellulose | 1 |
| Magnesium stearate | 0.8 |

The following exemplifies a formulation useful for topical ophthalmic application.

EXAMPLE 4

| Ingredient | Concentration (% w/v) |
| --- | --- |
| Compound of formulae A-H | 0.001-2 |
| Benzododecinium Bromide | 0.01-0.015 |
| Boric Acid | 0.2-0.4 |
| Xanthan Gum | 0.5-0.7 |
| Edetate Disodium | 0-0.01 |
| Polysorbate 80 | 0.05 |
| Mannitol | q.s. to 250-300 mOsm. |
| NaOH/HCl | q.s. to pH 6-8 |
| Purified Water | q.s. to 100% |

EXAMPLE 5

An EgLN-3 inhibitor, Compound 1 below, was tested in cultured adult rat retinal ganglion cells (RGCs). It was shown to protect against glutamate-induced cytotoxicity.

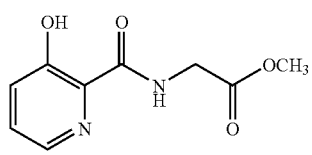

Compound 1

Methods

Adult Sprague-Dawley rats were euthanized by $CO_2$ asphyxiation. Their eyes were enucleated and the retinas isolated. Retinal cells were treated with of papain solution for 25 min at 37° C., then washed 3 times with 5 mL RGC culture medium (Neurobasal medium with various nutrient supplements+1% fetal calf serum). Retinal cells were dispersed by trituration. Cell suspension was placed onto poly-D-lysine- and laminin-coated 8-well chambered culture slides. The cells were then cultured in 95% air/5% $CO_2$ at 37° C.

For glutamate-induced toxicity studies, cells were pretreated with vehicle or the indicated compounds for 30 minutes, followed by 100 μM glutamate for 3 days. At the end of the incubation period, the cells were fixed and labeled for Thy-1, a RGC marker, by immunocytochemistry. Cell survival was quantified by manually counting Thy-1-positive healthy cells in each well.

Results

Only 70% of RGCs survived after a 3-day treatment of 100 μM glutamate. The graph of FIG. 1 shows that Compound 1, at 1 μM, was protective against this insult.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein.

What is claimed is:

1. A method for the treatment of a patient with ocular hypertension or glaucoma, which comprises administering to said patient in an ophthalmic formulation a pharmaceutically effective amount of a compound that inhibits the enzyme EgLN-3, and wherein the compound is selected from the group consisting of:

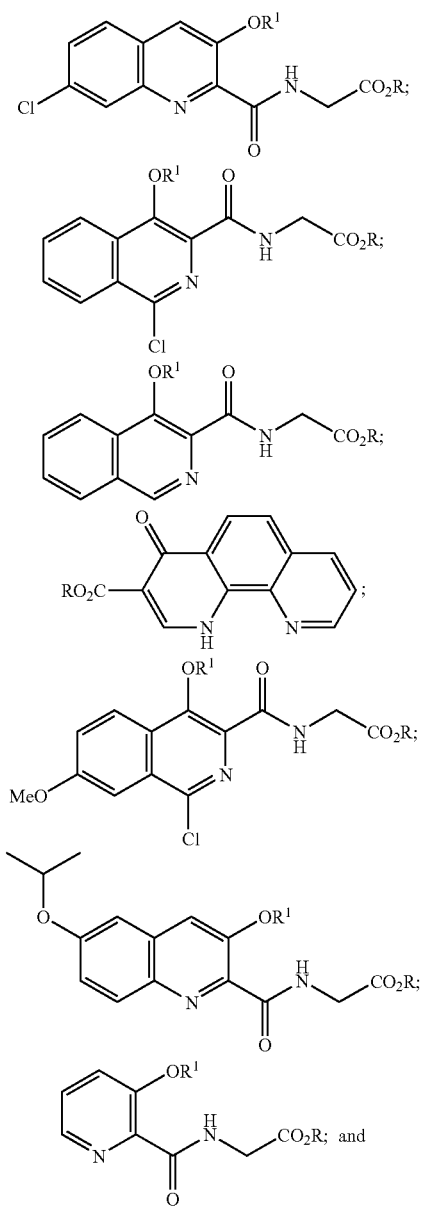

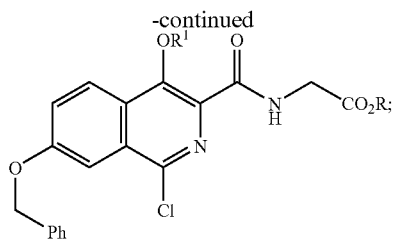

wherein:
R is H, $C_{1-6}$ straight chain or branched alkyl, phenyl, or benzyl, or $CO_2R$ forms a salt of formula $CO_2^-M^+$, with $M^+$ being $Li^+$, $Na^+$, $K^+$, or $NH_4^+$; and
$R^1$ is H, $C(O)CH_3$, or $C(O)C_6H_5$.

2. The method of claim 1, wherein the compound is selected from the group consisting of:

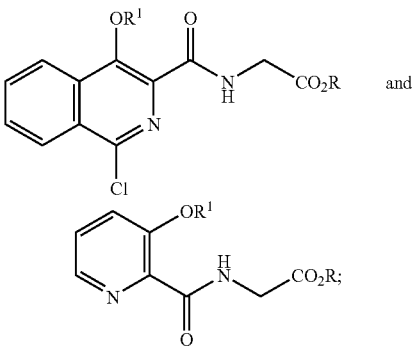

wherein:
R is H, H, $CH_3$, $C_2H_5$, or i-$C_3H_7$; and
$R^1$ is H or $C(O)CH_3$.

3. The method of claim 1, wherein the compound is administered in an implant.

4. The method of claim 1, wherein the compound is administered as an intraocular injection.

5. The method of claim 1 wherein the compound is administered topically to the eye in a composition comprising a pharmaceutically acceptable carrier.

6. The method of claim 5 wherein the pharmaceutically effective amount of the compound in the composition is from 0.001 to 2% (w/v).

7. The method of claim 6 wherein the pharmaceutically effective amount is from 0.01 to 1% w/v).

8. The method of claim 5, wherein the pharmaceutically acceptable carrier comprises one or more ingredients selected from the group consisting of surfactants; tonicity agents; buffers; preservatives; co-solvents; gelling agents, vehicles, water, penetration enhancers, and viscosity building agents.

9. The method of claim 1 wherein said administering further comprises administering said one or more compounds together with or separate from at least one glaucoma treatment agent selected from the group consisting of:
β-blockers, prostaglandin analogs, carbonic anhydrase inhibitors, $α_2$ agonists, miotics, rho kinase inhibitors and neuroprotectants.

* * * * *